US010588808B2

(12) United States Patent
Wheeler

(10) Patent No.: US 10,588,808 B2
(45) Date of Patent: Mar. 17, 2020

(54) STABILIZATION SYSTEM

(71) Applicant: Andrew Wheeler, Williamsville, NY (US)

(72) Inventor: Andrew Wheeler, Williamsville, NY (US)

(*) Notice: Subject to any disclaimer, the term of this patent is extended or adjusted under 35 U.S.C. 154(b) by 0 days.

(21) Appl. No.: 16/136,495

(22) Filed: Sep. 20, 2018

(65) Prior Publication Data

US 2019/0015240 A1     Jan. 17, 2019

Related U.S. Application Data

(63) Continuation-in-part of application No. 15/044,130, filed on Feb. 16, 2016, now abandoned, which is a (Continued)

(51) Int. Cl.
*A61G 13/00* (2006.01)
*A61F 5/37* (2006.01)
(Continued)

(52) U.S. Cl.
CPC .......... *A61G 13/009* (2013.01); *A61F 5/3707* (2013.01); *A61F 5/3761* (2013.01); *A61F 5/3769* (2013.01); *A61G 13/10* (2013.01); *A61G 13/101* (2013.01); *A61G 13/12* (2013.01); *A61H 1/008* (2013.01); *A61H 1/0222* (2013.01); *A61H 37/00* (2013.01); *A61B 6/0421* (2013.01); *A61G 13/0036* (2013.01); *A61G 2210/70* (2013.01);
(Continued)

(58) Field of Classification Search
CPC .... A61F 5/3769; A61F 5/3707; A61F 5/3761; A61H 37/00; A61H 2201/025; A61H 2201/0138; A61H 2201/0192; A61H 2201/1647; A61H 1/008; A61H 1/0222; A61H 1/0229; A61H 2203/0443; A61G 13/10; A61G 13/12; A61G 13/1205; A61G 13/101; A61G 13/121; A61G 13/122; A61G 13/1225; A61G 13/123; A61G 13/1245; A61G 13/125; A61G 13/1255; A61G 13/126; A61G 13/128; A61G 13/1295; A61G 13/009; A61G 13/0036; A61G 2210/70; A61G 2210/90; A61B 6/0421
See application file for complete search history.

(56) References Cited

U.S. PATENT DOCUMENTS 2,535,559 A * 12/1950 Monroe .................. A61G 13/12
5/621
3,238,936 A * 3/1966 Siedentop ............... A61F 7/007
601/19
(Continued)

*Primary Examiner* — David R Hare
(74) *Attorney, Agent, or Firm* — Phillips Lytle LLP

(57) ABSTRACT

A stabilization system configured to be arranged on a floor comprising a table having generally flat surface having a longitudinal axis for receiving a human body having a first hole, a second hole, and third hole within the flat surface, each hole having a hole shape with a generally vertical inner surface and configured to receive a bolster connector, a bolster comprising a bolster connector 'having an outer shape corresponding to the hole shape, the bolster connector configured to be reversibly engaged by one of the holes, a generally flat surface generally perpendicular to the table surface when the bolster connector is engaged by one of the holes.

20 Claims, 13 Drawing Sheets

Related U.S. Application Data continuation of application No. 14/305,031, filed on Jun. 16, 2014, now abandoned, which is a continuation of application No. 13/684,466, filed on Nov. 23, 2012, now abandoned.

(60) Provisional application No. 61/562,582, filed on Nov. 22, 2011.

(51) Int. Cl.
    *A61H 37/00*      (2006.01)
    *A61H 1/02*      (2006.01)
    *A61H 1/00*      (2006.01)
    *A61G 13/12*      (2006.01)
    *A61G 13/10*      (2006.01)
    *A61B 6/04*      (2006.01)

(52) U.S. Cl.
    CPC .. *A61G 2210/90* (2013.01); *A61H 2201/0138* (2013.01); *A61H 2201/0192* (2013.01); *A61H 2201/025* (2013.01); *A61H 2201/1647* (2013.01); *A61H 2203/0443* (2013.01)

(56) References Cited

U.S. PATENT DOCUMENTS

| | | | | |
|---|---|---|---|---|
| 3,434,165 A * | 3/1969 | Keane | .................. | A61F 5/3769 5/109 |
| 3,829,079 A * | 8/1974 | Fox | .................. | A61H 1/00 128/870 |
| 5,096,173 A * | 3/1992 | Yamashita | .................. | A61F 5/3769 5/621 |
| 5,289,603 A * | 3/1994 | Kumagai | .................. | A61G 7/065 128/869 |
| 5,360,392 A * | 11/1994 | McCoy | .................. | A61F 5/02 5/621 |
| 6,073,284 A * | 6/2000 | Borders | .................. | A61F 7/007 5/600 |
| 6,311,349 B1 * | 11/2001 | Kazakia | .................. | A61G 13/12 128/845 |
| 6,948,501 B2 * | 9/2005 | Rastegar | .................. | A61H 9/0078 128/845 |
| 7,100,225 B1 * | 9/2006 | Bailey | .................. | A61G 13/12 5/621 |
| 7,415,741 B1 * | 8/2008 | Wasley | .................. | A61G 13/12 5/621 |
| 7,694,369 B2 * | 4/2010 | Hinders | .................. | A61G 13/12 5/613 |
| 7,740,015 B2 * | 6/2010 | Hyde | .................. | A61F 5/05 128/845 |
| 7,836,890 B2 * | 11/2010 | Waterman | .................. | A61B 6/0421 108/1 |
| 8,146,189 B2 * | 4/2012 | Yang | .................. | A61B 6/0457 5/616 |
| 8,393,329 B2 * | 3/2013 | Snow | .................. | A61G 13/12 128/845 |
| 8,914,922 B1 * | 12/2014 | Wells | .................. | A61G 13/009 5/423 |
| 2002/0170116 A1 * | 11/2002 | Borders | .................. | A61B 6/0457 5/600 |
| 2014/0201917 A1 * | 7/2014 | Neel | .................. | A61G 13/126 5/621 |

\* cited by examiner

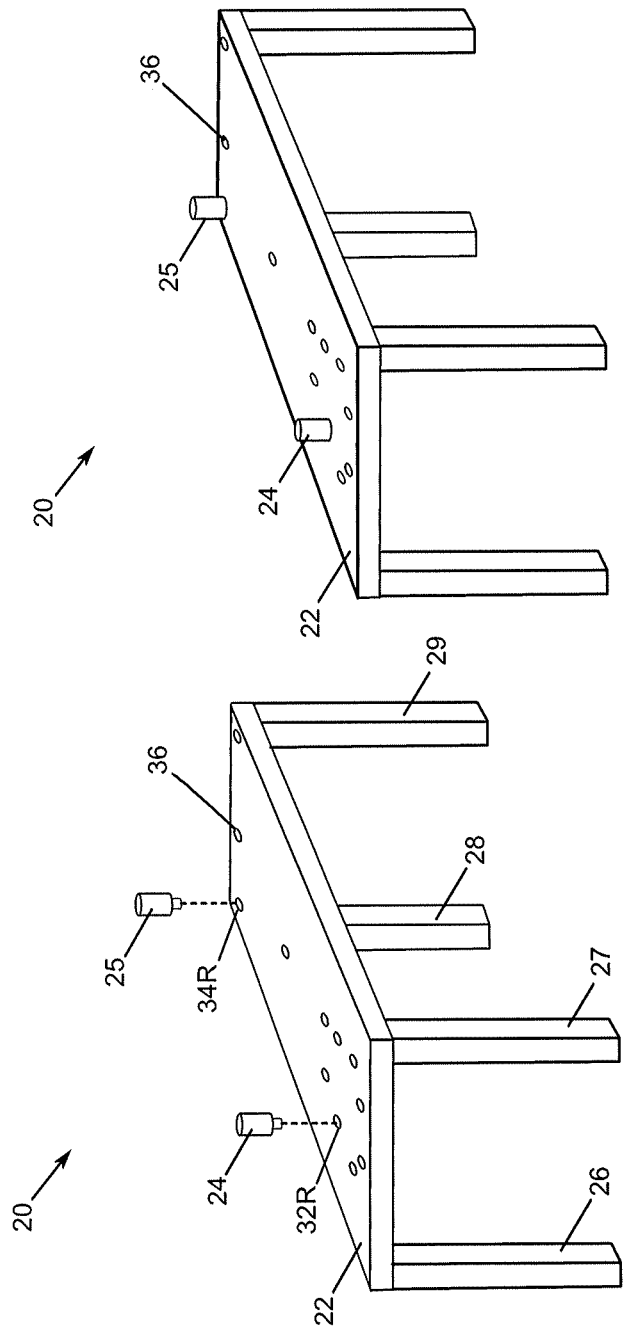

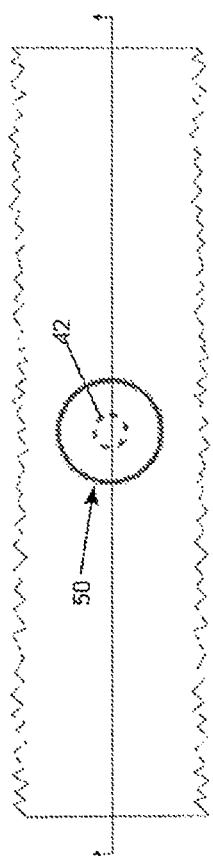
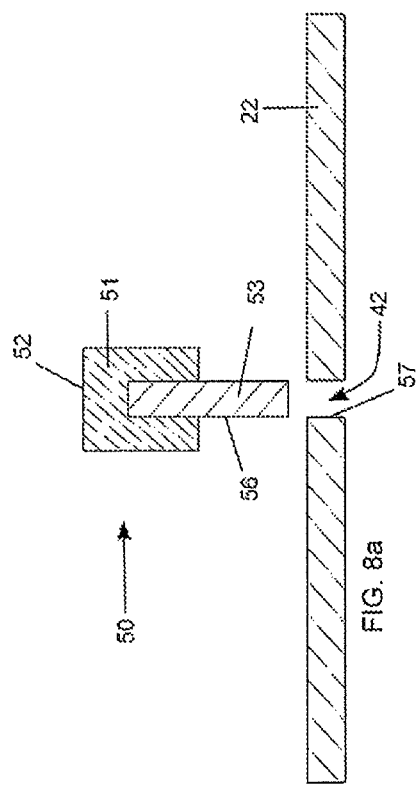
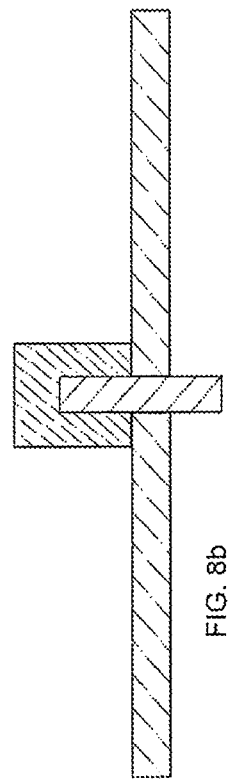
FIG. 7
FIG. 8a
FIG. 8b

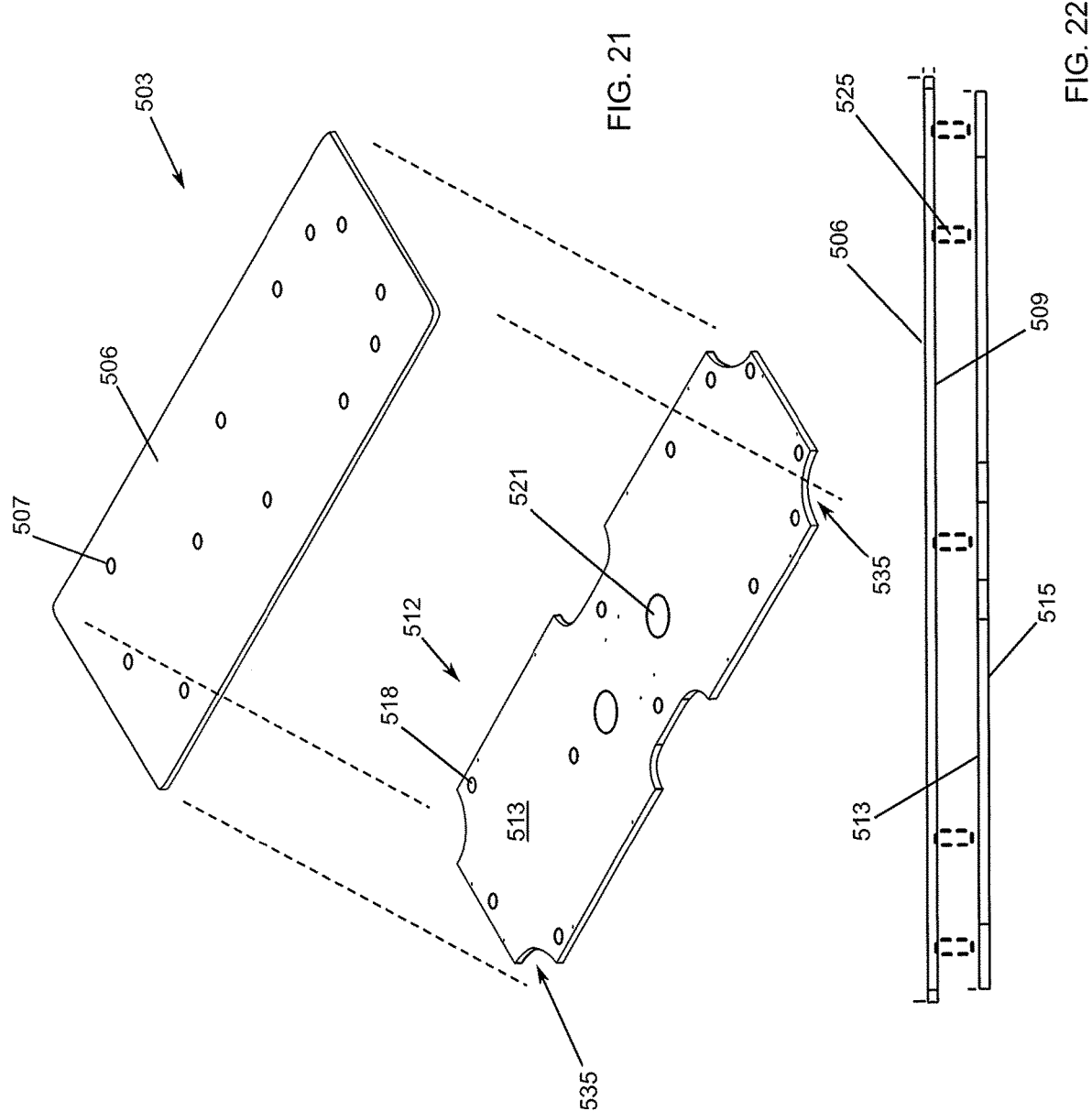

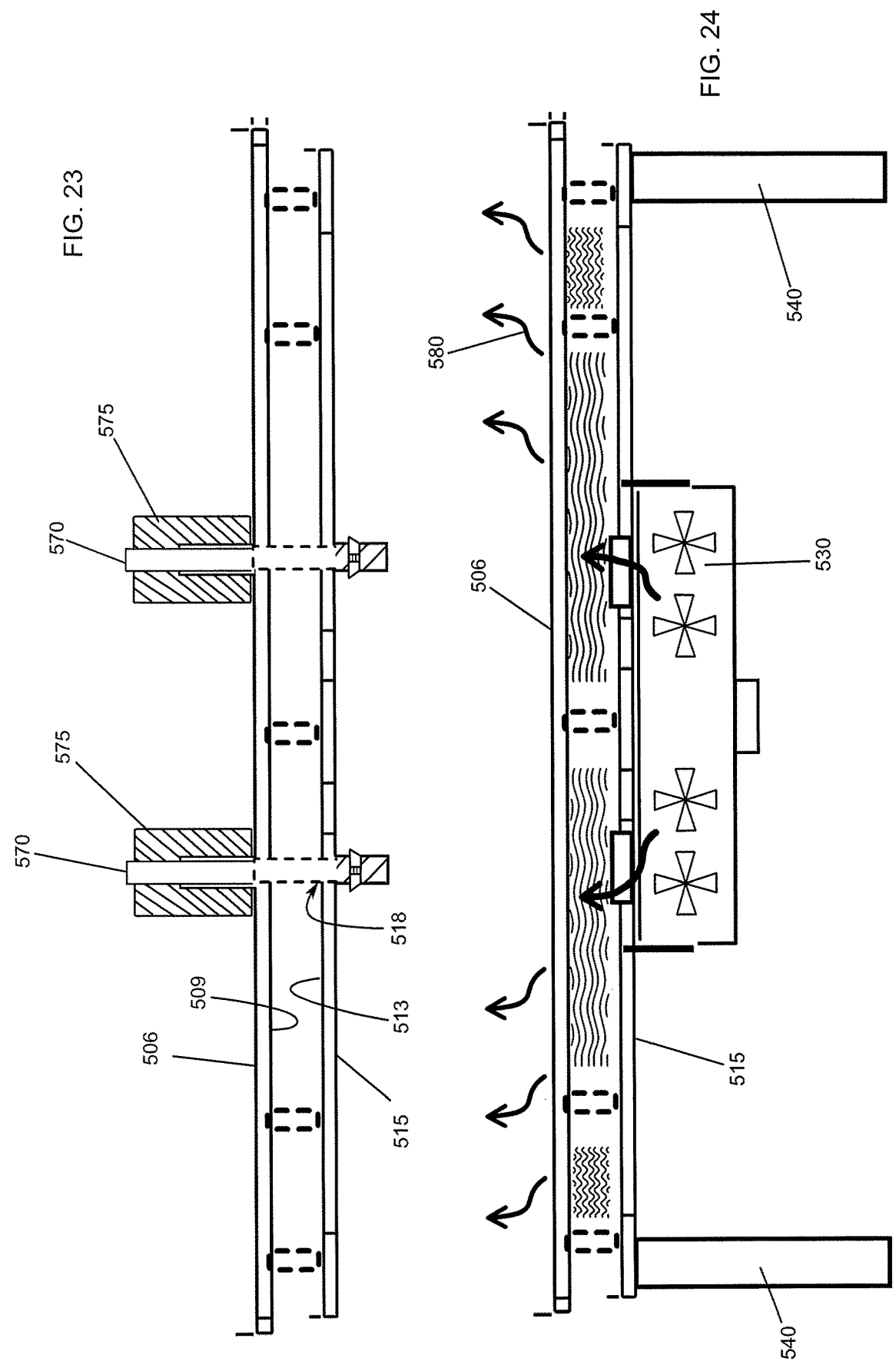

STABILIZATION SYSTEM

CROSS-REFERENCE TO RELATED APPLICATIONS

The present application is a continuation-in-part application of U.S. patent application Ser. No. 15/044,130, filed Feb. 16, 2016, which is a continuation of U.S. patent application Ser. No. 14/305,031, filed Jun. 16, 2014, which is a continuation of U.S. patent application Ser. No. 13/684,466, filed Nov. 23, 2012, which claims the benefit of U.S. Provisional Application No. 61/562,582, filed Nov. 22, 2011, which, each of which is hereby incorporated by reference.

TECHNICAL FIELD

The present invention relates generally to a stabilization system and, more particularly, to a stabilization system for physical therapy.

BACKGROUND ART

Tables for the stabilization of a human body are generally known. U.S. Pat. App. No. 2009/0235461 is directed to an Infant Sleep Positioner and discloses a frame with releasable bolsters to support an infant. U.S. Pat. No. 7,308,725 entitled "Deployable and/or Retractable Mattress Bolsters" discloses a therapeutic bed having a mattress with fluid cushion and retractable/deployable bolsters protruding from a top surface. U.S. Pat. No. 7,614,098 is directed to a support system having an elastomeric mesh and a plurality of bolsters repositionably securable to the mesh.

BRIEF SUMMARY OF THE INVENTION

With reference to the corresponding parts, portions or surfaces of the disclosed embodiment, merely for purposes of illustration and not by way of limitation, provided is a stabilization system configured to be arranged on a floor comprising: a table having generally flat surface having a longitudinal axis for receiving a human body having: a first hole, a second hole, and third hole within the flat surface, each hole having a hole shape with a generally vertical inner surface and configured to receive a bolster connector; a bolster comprising: a bolster connector having an outer shape corresponding to the hole shape; the bolster connector configured to be reversibly engaged by one of the holes; a generally flat surface generally perpendicular to the table surface when the bolster connector is engaged by one of the holes.

The first hole and the second hole may be arranged opposite each other along the longitudinal axis and may be separated from each other by a width selected such that when the first hole is connected to a first bolster and the second hole is connected to a second bolster a human head fits between the bolsters without free space between the first and second bolsters. The first hole and the second hole may be generally aligned on either side of a neck of the body.

The stabilization system may further have two holes aligned on either side of a hip region of the body, two holes aligned on either side of an armpit region of the body, two holes aligned on either side of a waist region of the body, two holes aligned on either side of a knee region of the body, and/or two holes aligned on either side of an ankle region of the body.

The table may be configured to a support a lateral force greater than 20 lbs. on one of the bolsters. The bolster vertical surface may have a height of at least 6". The bolster may have a cross section shape that is a circle, triangle, or rectangle. The bolster may have a low shear surface.

The holes may be cylindrical holes and/or the connector may have a cylindrical shape corresponding to the diameter of the cylindrical holes. The connector may be configured to allow the bolster to rotate relative to the table. The holes may be non-cylindrical holes and the connector may have a non-cylindrical shape corresponding to the size of the non-cylindrical holes.

The connector may have a lock for locking the bolster into one of the holes.

The stabilization system may further have a plurality of bolsters.

In another aspect, a stabilization table is provided which is configured to be arranged on a floor comprising a generally flat surface having a longitudinal axis for receiving a human body having a first hole, a second hole, and third hole within the flat surface, each hole having a hole shape with a generally vertical inner surface and configured to receive a bolster connector, a bolster having, a generally vertical surface for contacting a body part, a connection means for reversibly attaching the bolster to one of the holes.

The bolster may have a cross section shape that is a circle, triangle, or rectangle. The connector may have a lock for locking the bolster into one of the holes. The human body may be a child body or an adult body.

In another aspect, provided is a stabilization system configured to be arranged on a floor having: a generally flat surface with a longitudinal axis for receiving a human body with a plurality of holes and bolster having a bolster connector configured to engage one of the holes. Each hole having a hole shape with a generally vertical inner surface. A first hole and second hole are generally aligned on either side of a neck of the body. The bolster having a generally vertical surface for contacting a body part, and the bolster connector having an outer shape substantially corresponding the shape of the holes, and where the connector is configured to be reversibly engaged by one of the holes.

The stabilization system may also have two holes aligned on either side of a corresponding hip region of a body. The system may have two holes aligned on either side of a corresponding armpit region of a body. The system may have two holes aligned on either side of a corresponding on either side of a waist region, knee region, or ankle region of a body.

The stabilization system may have its holes specifically configured to a support a lateral force greater than 20 lbs.

The generally flat surface of the stabilization system may have a length between 3 feet and 7 feet and a width between 2 feet and 3 feet. The flat surface may have an elevation height of approximately 32". The flat surface may have a padding layer. The flat surface may be made of a substantially solid substance, or may be made of a fluid substance.

The outer portion of the flat surface may configured to be disinfectable with liquid cleansers. The flat surface may be made of nonporous material and may be vinyl or another similar material. The surface of the flat surface may be a low shear surface.

The stabilization system may have bolsters with a bolster vertical surface of at least 4" high. The bolster may have an outer shape that is generally a cylinder, a triangular prism, or a rectangular prism.

The outer surface of the bolster may configured to be disinfectable with liquid cleansers. The outer surface of the bolster may be made of nonporous material and may be vinyl or another similar material. The outer surface of the bolster may be a low shear surface.

The bolster may be made of a substantially solid material. The bolster may contain padding and may be made of foam.

The bolster connector may be made of metal, wood, or PVC. The connector may be configured for fast insertion and fast removal from the stabilization table holes. The connector may be specifically configured to support a lateral force of greater than 20 lbs.

The stabilization system table holes may be cylindrical holes and the connector may have a cylindrical shape corresponding to the diameter of the cylindrical holes. The connector and holes may have a shape with a non-circular cross section. The connector and holes may have a triangular, square, or hexagonal cross section.

The connector or holes may be configured to allow the bolster to be rotate within the holes. The bolster connector or stabilization table holes may have a locking mechanism for locking the bolster into one of the holes. The locking mechanism may include a spring and a latch. The locking mechanism may contain a release button. The release button may be arranged on top of the bolster. The stabilization table holes may be configured to compressively engage the bolster connector.

The stabilization table may be configured to not move when in use. The stabilization table may have legs which can fold up. The legs may have angle brackets and the brackets may be configured to prevent rocking. The legs may have rubber stoppers on their ends to prevent sliding. The legs may be comprised of a stiff material and may contain screw-in bottoms on its legs to allow for height adjustment.

The stabilization system may be provided with a plurality of bolsters and a plurality of bolsters may be used at the same time.

In another aspect, a stabilization system is provided having a table configured to be arranged on a floor having: a generally flat surface with a longitudinal axis for receiving a human body with a first hole, a second hole, and third hole within the flat surface, each hole having a hole shape with a generally vertical inner surface and configured to receive a bolster connector. The bolster having a generally vertical surface for contacting a body part; a bolster connector with an outer shape substantially corresponding the table hole shapes; and the bolster connector configured to be reversibly engaged by one of the holes; in which the first hole and second hole are arranged opposite each other along the longitudinal axis and are separated from each other by a width selected such that when the first hole is connected to a first bolster and the second hole is connected to a second bolster a human head fits without free space between the first and second bolsters.

In an another aspect, a stabilization system is provided having a table configured to be arranged on a floor and having: a generally flat surface with a longitudinal axis for receiving a human body having a first hole, a second hole, and third hole within the flat surface, each hole having a hole shape with a generally vertical inner surface and configured to receive a bolster connector, and the first hole and second hole generally aligned on either side of a neck of a body. The system further having a bolster having a generally vertical surface for contacting a body part and a connection means for reversibly attaching the bolster to one of the holes.

BRIEF DESCRIPTION OF THE DRAWINGS

FIG. 1 is an exploded perspective view of a first embodiment stabilization system.

FIG. 2 is a perspective view of the first embodiment stabilization system.

FIG. 7 is a top a view of a portion of the first embodiment stabilization system.

FIG. 8a is a front sectional view of the first embodiment stabilization system.

FIG. 8b is a front sectional view of the first embodiment stabilization system.

FIG. 21 is an exploded perspective view of an alternate embodiment of the invention having a planar member supported below the top surface of the table.

FIG. 22 is an elevational view of the table assembly of FIG. 21;

FIG. 23 is an elevational view of the assembly of FIG. 22 with a pair of bolsters installed therein;

FIG. 24 is an elevational view of the alternate embodiment table assembly of FIGS. 21-23 with a fan disposed beneath the planar member to provide air flow into the cavity formed between the bottom surface of the table top and the top surface of the planar member;

DETAILED DESCRIPTION OF THE PREFERRED EMBODIMENTS

Figure 4:
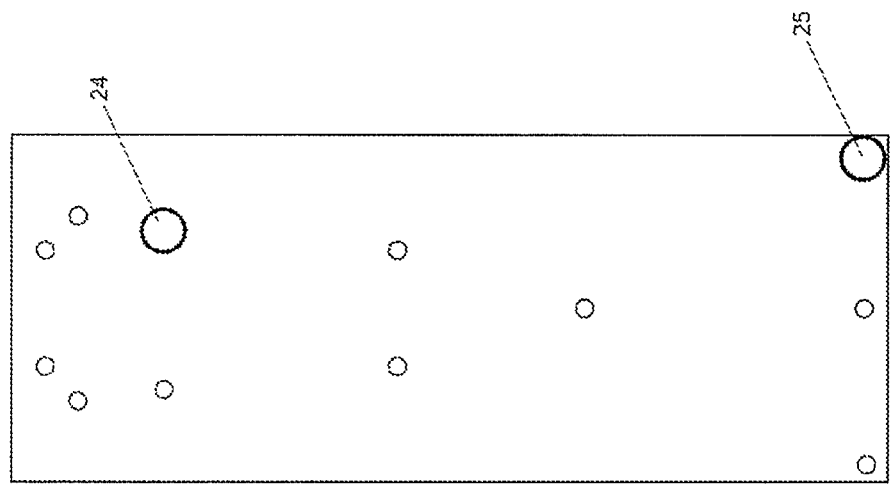
FIG. 4 is a top view of the first embodiment stabilization system.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, and more particularly to FIGS. 1, 2, thereof, provided is a stabilization system, a first embodiment of which is generally indicated at 20. System 20 generally has a table 21 having a plurality of holes (for example 32R, 34R) into which a number of bolsters (for example 24, 25) are arranged to provide support to patient 90 (shown in FIG. 16) during a therapy session.

As shown in FIGS. 1-4, table 21 has a generally flat surface 22 which is held generally parallel to the ground by table legs 26, 27, 28, and 29. Table 21 has a number of vertical circular holes, such as holes 32R, 34R, and 36. The circular holes have an inner cylindrical wall which is generally perpendicular to the generally flat surface 22 of table 21. Each hole is substantially the same shape as the other holes. Each hole is configured to be able to reversibly receive a bolster, such as bolster 24 and bolster 25. As shown in FIGS. 1 and 2, hole 32R receives bolster 24 and hole 34R receives bolster 25. Bolsters 24 and 25 are substantially identical, each bolster having a generally cylindrical body.

Figure 3:
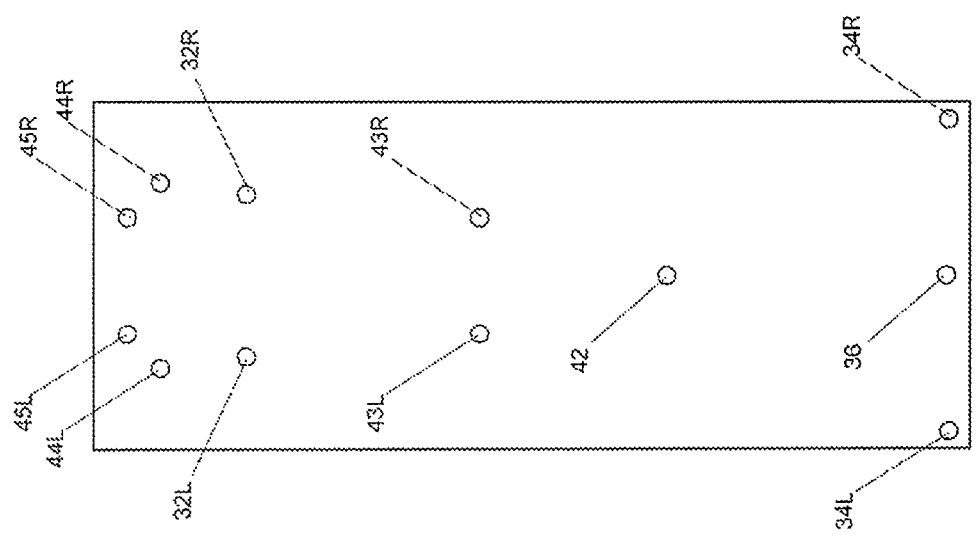
FIG. 3 is a top view of the table portion of the first embodiment stabilization system.

FIG. 3 is a top view of table 21 showing the arrangement of holes. The hole arrangement is symmetrical about a vertical central axis as viewed in FIG. 3. Each hole on the left side of the central axis has a corresponding hole on the right side of the central axis. For example, hole 45L is located on the left side of the central vertical axis relative to hole 45R on the right side of the central axis. The position of the holes are arranged to generally align with major body regions of person 90. For example, holes 45L and 45R are arranged to generally align on the left and right sides of person 90's head. Holes 44L and 44R are arranged to generally align with either the sides of person 90's head or the upper shoulders of person 90. Holes 32L and 32R are arranged to generally align with the torso and lower shoulders (arm pit region) of person 90. Holes 43L and 43R are generally arranged to align with the left and right torso or hip regions of person 90. Hole 42 is generally arranged to align with the region between person 90's knees. Hole 36 is generally arranged to align with the region between (medial to) person 90's ankles; and holes 34L and 34R are generally arranged to align with the outer (lateral) left and right sides of person 90's ankles.

FIG. 4 is a top view of stabilization system 20 of FIG. 2, with bolster 25 arranged in hole 34R and bolster 24 arranged in hole 32R.

Figure 6:
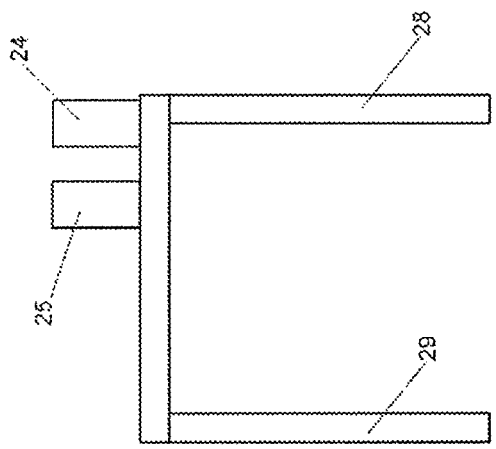
FIG. 6 is a front view of the first embodiment stabilization system.
Figure 5:
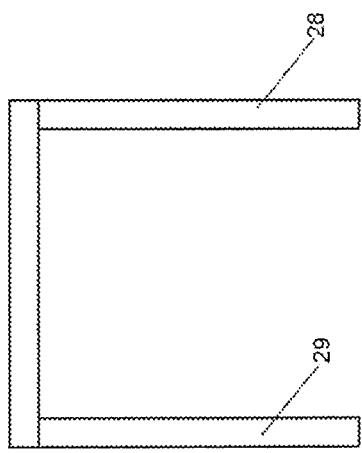
FIG. 5 is a front view of the table portion of the first embodiment stabilization system.

FIG. 5 is a front view of table 21 of system 20 showing how legs 28 and 29 are arranged vertically and are attached to generally flat surface 22. FIG. 6 is a front view of stabilization system 20 in the same configurations as FIG. 2 and FIG. 4, with bolster 25 arranged in hole 34R and bolster 24 arranged in 32R.

FIG. 7 is a top a view of a close up portion of the first embodiment stabilization system in a configuration with bolster 50 arranged over hole 42 prior to insertion. FIG. 8*a* is an exploded front section view taken along the section line in FIG. 7. As shown in FIG. 8*a*, bolster 50 is comprised of a casing 52, an inner material 51, and a connector 53. Casing 52 is made of vinyl, inner material 51 is made of foam, and connector 53 is made of metal. As shown in the figures, bolster 50 is generally the shape of two concentric cylinders attached end to end, casing 52 forming the outer boundary of a first larger cylinder, attached to connector 53 forming a cylinder of a smaller diameter. Inner material 51 fills the space between casing 52 and connector 53.

FIG. 8*b*, is a front section view of bolster 50 inserted into hole 42. Bolster 50 fits into hole 42 with little clearance. More specifically, hole 42 has a cylindrical shape with a slightly smaller diameter than the diameter of connector 53. This allows connector 53 to vertically slide into hole 42. Vertical surface 56 of connector 53 slidably engages vertical surface 57 of hole 42. The diameters of connector 53 and hole 42 are held in tight tolerance; because of the small difference in the diameters, bolster 50 is unlikely to move laterally or wiggle when placed in hole 42. Each of the other holes in table 21 are of the same shape as hole 42. This allows bolster 50 to be easily placed in any of the holes in table 21. Similarly, bolsters 24 and 25 are substantially equivalent to bolster 50, allowing each bolster of the first embodiment to fit in any of the table 21 holes of the first embodiment.

Figure 9:
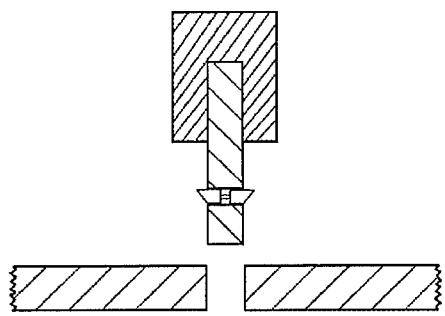
FIG. 9 is a front sectional exploded view of a bolster and table portion of the first embodiment stabilization system.
Figure 10:
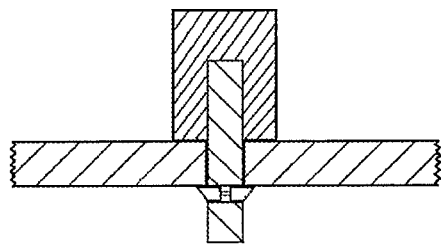
FIG. 10 is a front sectional view of a bolster and table portion of the first embodiment stabilization system.

FIGS. 9 and 10 show bolster modified bolster connector design which allows the bolster to lock within a stabilization table hole. Latches 54L and 54R are arranged within connector slot 155 and configured to slide horizontally within a range within the connector slot. Bias element 156 urges latches 154L and 154R radially outwards within connector slot 155. As bolster 150 is pressed into a stabilization table hole, latches 154L and 154R are forced radially inwards by the stabilization table hole. As the modified connector exits the lower exit of the stabilization hole, latches 54L and 54R are free to slide radially outwards, locking the bolster to the stabilization table as shown by the configuration in FIG. 10. Bolster 150 as shown in FIG. 10 can be released by manually pressing latches 154R and 154L radially inwards while pulling bolster 150 vertically upwards out of the table hole.

Figure 11:
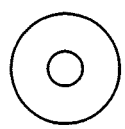
FIG. 11 is a top a view of a bolster of the first embodiment stabilization system.
Figure 12:
FIG. 12 is a top a view of a bolster of a second embodiment stabilization system.
Figure 13:
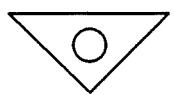
FIG. 13 is atop a view of a bolster of a third embodiment stabilization system.
Figure 14:
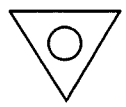
FIG. 14 is a top a view of a bolster of a fourth embodiment stabilization system.

FIGS. 11-14 show several bolster designs with modified casing shapes. FIGS. 11 and 12 show bolster designs with an enlarged and reduced outer diameters respectively. FIG. 13 discloses a bolster with a right triangular prism shape. FIG. 14 discloses a bolster with an equilateral triangular prism shape. Each of the different bolster types have a slightly different outer vertical surface which may be more appropriate for interfacing with patient 90 depending upon the body region which is to be interfaced, or the type of therapy which is to be provided.

Figure 15:
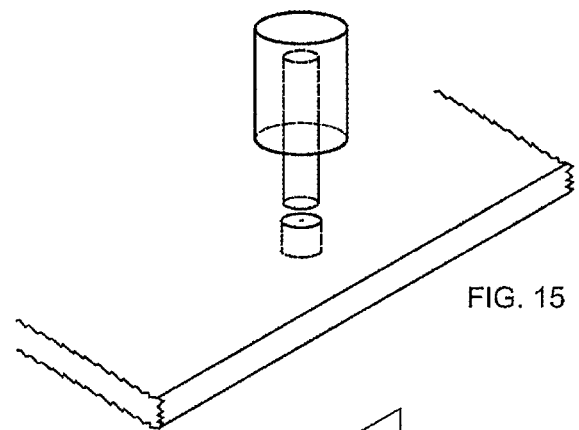
FIG. 15 is a perspective exploded view of the first embodiment stabilization system.
Figure 16:
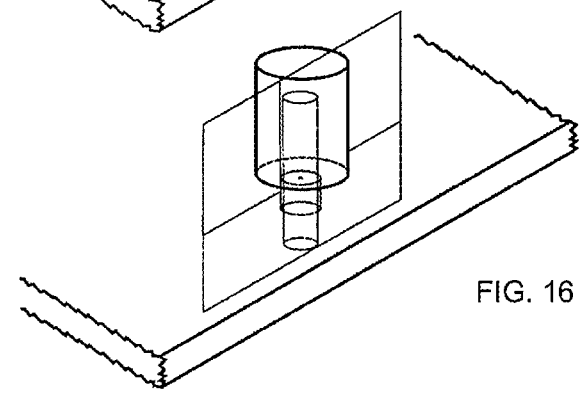
FIG. 16 is a exploded view of the first embodiment stabilization system in a bolster attached configuration
Figure 17:
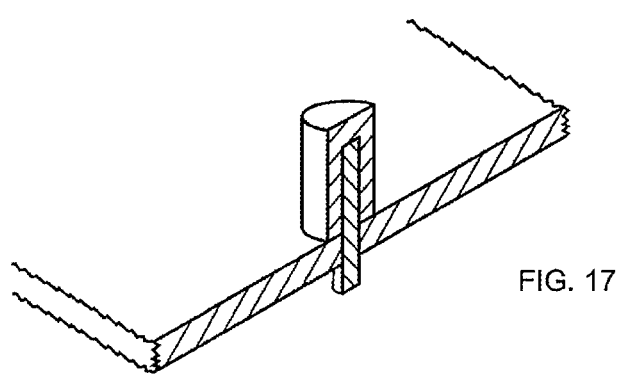
FIG. 17 is a perspective section view taken along the section plane shown in FIG. 16.

FIGS. 15-16 provided perspective views of the insertion of a bolster into a table hole. More specifically, FIG. 15 is a perspective view of the bolster arranged above a table hole. FIG. 16 is a perspective view of the bolster after being inserted into the table hole. FIG. 17 is a perspective section view taken along the section plane shown in FIG. 16.

Figure 18:
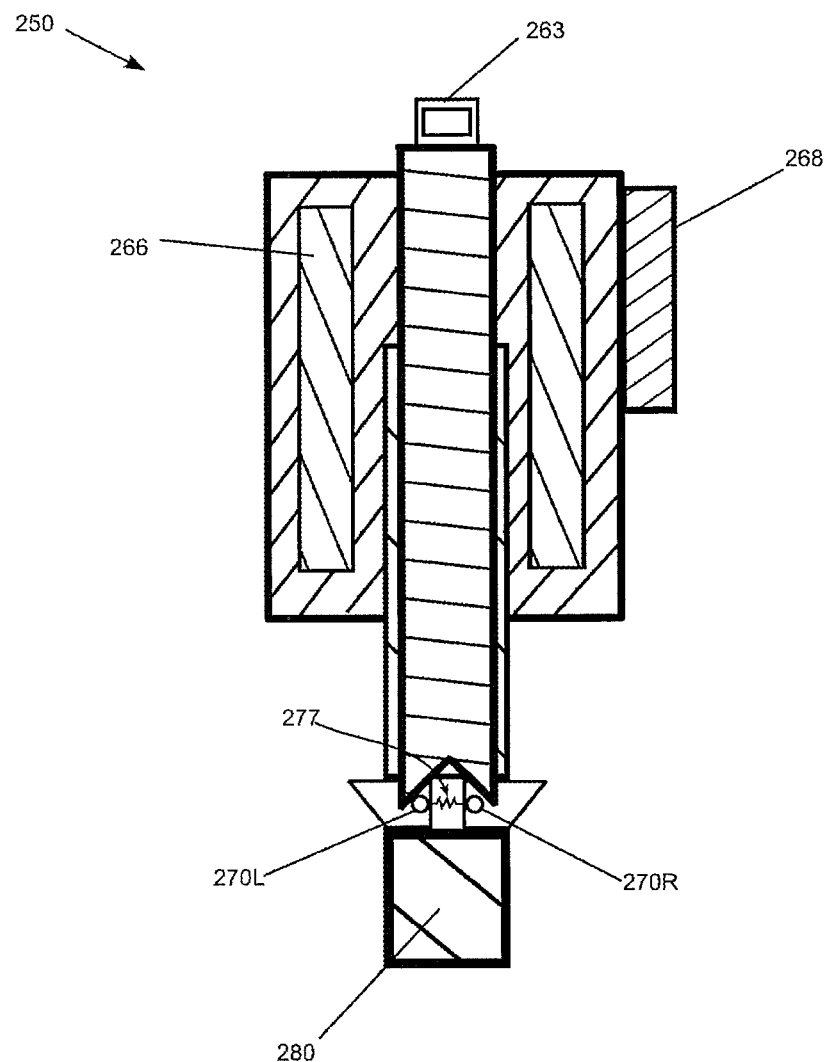
FIG. 18 is a perspective view of a fifth embodiment stabilization system.

FIG. 18 is a sectional view of another embodiment bolster 250. Bolster 250 is generally similar in shape and design as bolster 50, with some additional elements. Bolster 250 has hook 263 arranged on the upper end of bolster 250. Hook 263 provides a connection point for an elastic resistance member which may be used during therapy. Bolster 250 also has inner temperature member 266. Temperature member 266 is used for causing bolster 250 to be at a temperature different than the ambient temperature. In one form, temperature member 266 is an electric resistive coil for converting electricity into heat. In another form, temperature member 266 is a bladder holding a high specific heat material such as water. The water bladder allows the bolster to be placed into a freezer or heated bath prior to treatment, such that when bolster 250 is placed on the table during treatment, it retains its different than ambient temperature for an extended period of time. Bolster 250 also has dynamometer 268 for indicating the magnitude of an external force that is applied to bolster 250. Dynamometer 268 has a digital display for showing the force placed against the bolster surface as the bolster is held in position by a table hole. The digital display may also display the duration that the force was applied. The dynamometer used in this embodiment is a Hoggan Scientific, LLC, microFET dynamometer, however other similar dynamometers may be alternatively be used.

Figure 20:
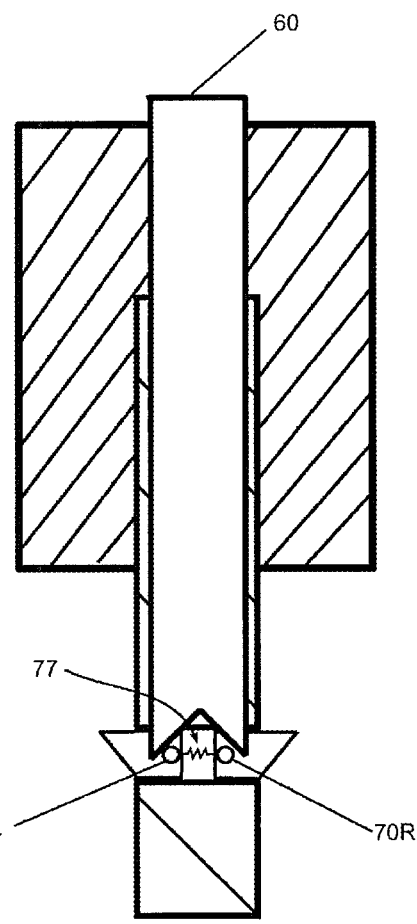
FIG. 20 is a front sectional view of a lock and release mechanism for a bolster in a sixth embodiment stabilization system.
Figure 25:
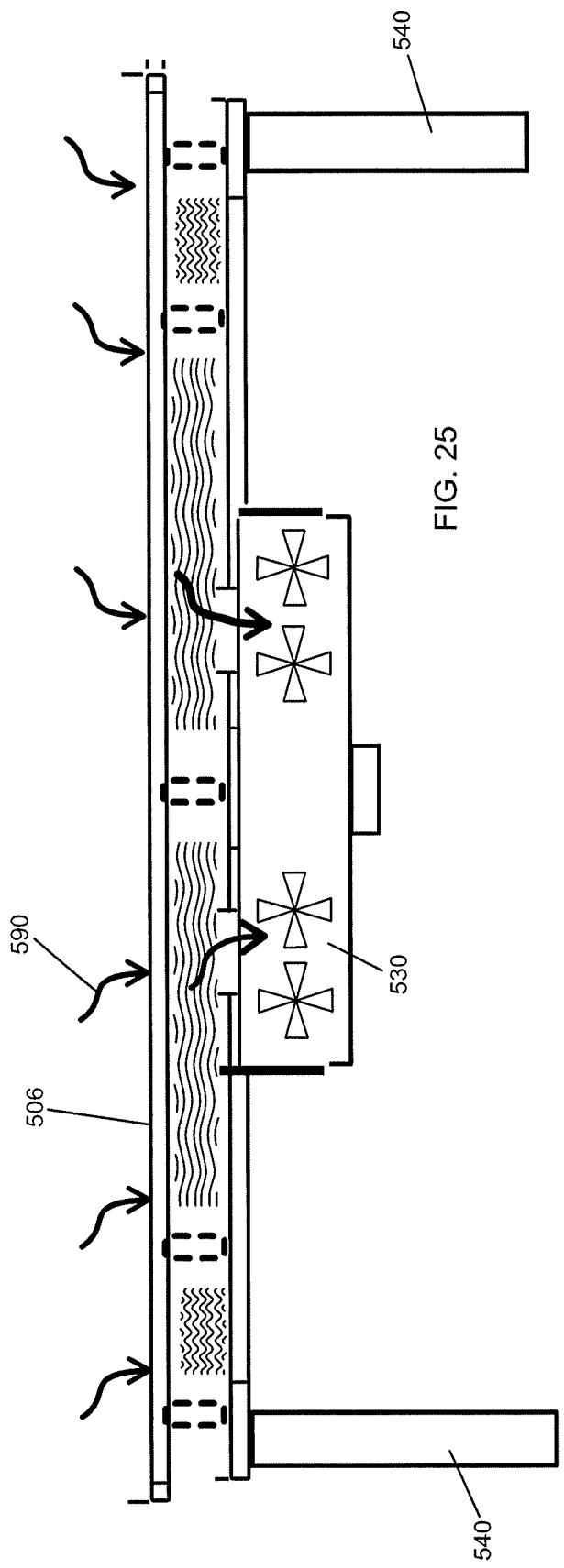
FIG. 25 is an elevational view of the assembly shown in FIG. 24 with the direction of the air flow reversed; and, FIG. 26 is a top perspective view of a user supported on the top surface of the table top for the system shown in FIG. 25.

FIG. 20 is a sectional view of another design for a modified bolster connector having a release button. As shown in FIG. 20, release button 60 has a downwardly extending body with an angled bottom edge. The angled bottom edge engages latch nubs 70R and 70L. When release button 60 is pressed downwards, the angled bottom edge acting on nubs 70R and 70L forces the latches to move radially inwards, allowing a user to remove the bolster for a stabilization table hole.

Each embodiment stabilization system may be used with bolsters placed in any number of holes in table 21. Bolsters of different shape may be used at the same time.

The operation of the stabilization system is as follows. A stabilization system without any bolsters attached is first positioned on a generally flat surface, such as a clinic room floor. A user next decides the type of activity that will be performed on with the stabilization system, such as a neck manipulation, and then determines the appropriate table hole(s) that will be used for bolster placement, such as holes 32R and 34R as shown in FIG. 3. Next, the user vertically aligns a bolster over an appropriate table hole, as shown in FIG. 15 and FIG. 8A. The user then pushes the bolster downwards until the bolster shaft portion 53 emerges from the lower side of the table hole and the bolster upper portion 51 contacts the upper surface of the table. This process is repeated for each bolster that user determines is needed, yielding a bolster mounted configuration as shown in FIG. 4.

Figure 19:
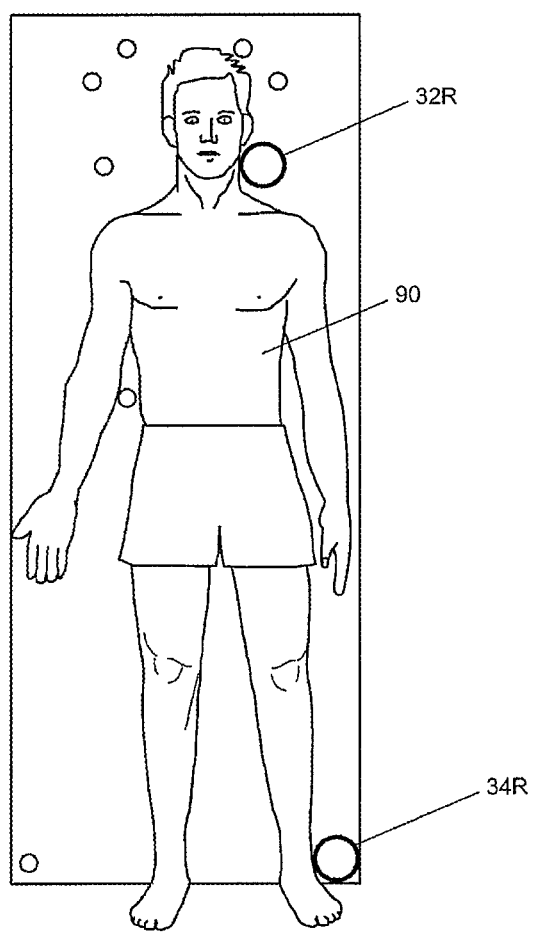
FIG. 19 is a top view of a patient arranged in the first embodiment stabilization system.

A patient is then arranged on the stabilization system table up against the mounted bolsters as shown in FIG. 19. A user then performs therapeutic manipulations on the patient, such as stretching, pushing, and pulling portions of the patient's body. Such therapeutic manipulations may be specific to physical therapy, chiropractic manipulations, athletic training, massage, orthopedic specialties, or other similar purposes. The bolsters offer support to counteract a user's manipulations. This allows a user to apply a directed force to a patient's body at various regions through the bolsters. During the session, the user may move a bolster from one hole to another hole. In addition, a user may add more bolsters as needed.

Typical clinical operation of the stabilization system would include one to multiple patient positions during any given therapeutic task. A clinician could instruct a patient to change their orientation respective to the table and bolsters once or many times throughout clinical encounters. One, none or many bolsters could be used during a clinical session dependent upon the desired outcome of that meeting. The bolsters may be used to (including but not limited to): fixate patients to allow forces to be imparted upon them (push or pull), resist patient muscle activity (voluntary or involuntary), fixate clinical accessories, impart counter gravitational force or assist in general gravity dependent positioning.

An additional embodiment of the stabilization system may have a stabilization table with holes that are not circular, and corresponding bolsters with connectors having a non-circular cross section. For example, hexagonal stabilization table holes and bolster connectors may be used. This would prevent the bolster from rotating within the stabilization table hole. This may be particularly advantageous with bolsters having non circular bolster casings.

Another embodiment contains bolsters which may be laterally combined to form a larger surface for interacting with a patient. Further bolster types may be bendable, and/or may have a magnetic connector in the bolster connector for holding the bolster to the table.

Another embodiment has stabilization table legs with fold up legs. Additionally, modified legs may have a screw foot which would allow slight adjustments to leg height to allow corrections on non-flat floors to prevent the table from rocking. The table may also have a scale incorporated into it. The scale allows both the patient weight to be determined, as well as provides a way of telling the user a way of determining how much vertical force is being applied during a therapy step.

Turning to FIGS. 21-26, an alternate table assembly 500 (FIG. 24) includes a table top 503 having a top surface 506 and a bottom surface 509. The top surface 506 may be provided with a plurality of openings 507. A planar member 512 having a top surface 513 and a bottom surface 515 is disposed such that the top surface 512 is disposed in spaced apart relation from the bottom surface 509 of the table top 503. The top surface 513 of the planar member 512 may be provided with a plurality of openings 518 that may align with some or all of the openings 507.

Figure 26:
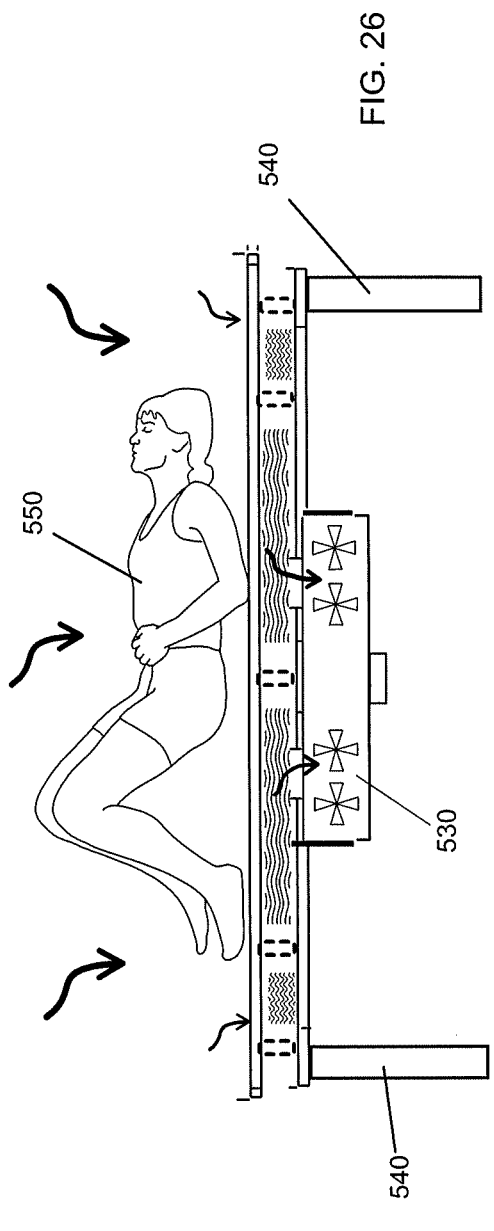

The top surface 513 of the planar member 512 may be spaced a distance between one and fifteen inches from the bottom surface 509 of the table top 503. The planar member 512 will mirror the table top 503 as it pertains to the openings 507 in the table top 503 for accepting bolsters. The planar member 512 may also have additional openings 521 that do not mirror the openings 507 in the top surface 506. Openings 518 or holes in the planar member 512 that mirror the top surface 506 of the table top 503 are sized to accept a bolster 570 that passes first through the top surface 506 of the table top 503. The bolster casing 575 is disposed above surface 506 for interface with user or subject 550 (FIG. 26). As best shown in FIG. 23, the openings 518 in the planar member 512 provide a counter force needed for stability when the bolster 570 has force imparted on it in any direction providing needed circumferential support at a necessary distance from the top surface 506 pivot point. The space between the bottom surface 509 of the table top 503 and the top surface 513 of the planar member 512 may contain support structures 525 to increase the stability, strength, and durability of the overall structure.

The planar member 512 and the table top 503 accommodate airflow from the top table surface and the bottom surface 515 of the planar member 512 through openings or arrangement of the surfaces to provide gaps for airflow.

The planar member 512 is provided with a plurality of specifically designed openings 521 that allow for connection to an air movement apparatus 530 such as a blower, fan or the like. There may also be openings 535 provided for receiving legs 540 to support the table. The air movement apparatus 530 may be powered by electricity via alternating current, battery power or manual operation. The air moving apparatus 530 generates airflow that can be either toward the top surface 506 of the table top 503 in the direction of arrow 590 (FIG. 25) or it may flow in the opposite direction away from the top surface 506 of the table top 503 in the direction of arrow 580 (FIG. 24). The airflow apparatus 530 is not limited to mechanical devices and may be constructed of any suitable material to facilitate air movement. The space between the bottom surface 509 of the table top 503 and the top surface 513 of the planar member 512 distributes the air flow toward or away from a subject positioned on the top surface 506 of the table top 503.

The airflow apparatus can be made to move any temperature air desired for heating or cooling of subjects on the top surface 506 of the table top 503.

Specific openings 535 may be located at the four corners of the table and centrally (along the long axis of the table embodiment) of the top surface of the planar member to accommodate attaching and detaching table legs to the table.

The openings 535 located at the four corners of the planar member 512 may be cut on a radius emanating from the corners of the table. The radius may be no less than two inches and no more than ten inches. The openings 521 located centrally on the top surface 513 of the planar member 512 may be cut using a rounded rectangular shape (also known as a stadium shape geometrically). The rounded corners of said rounded rectangle shape may be cut using a radius no less than two inches and no more than five inches. The long access of the rounded, rectangular shape may be no less than six inches and no more than twenty-four inches.

The cut openings allow for attachment and removal of table legs 540 while maintaining desired distance between the table top 503 and the planar member 512. The cut openings are sized to accommodate minimally-needed space for tool placement during attachment and removal of table legs 540, but maintain the structural integrity of the overall planar member 512.

While a preferred form of the stabilization system has been shown and described, and several modifications thereof discussed, persons skilled in this art will readily appreciate that various additional changes may be made without departing from the spirit of the invention, as defined and differentiated by the following claims.

What is claimed is:

1. A stabilization table configured to support a patient, the stabilization table comprising a generally flat upper surface for receiving a patient and a bottom surface, wherein the table has at least three holes, each with a generally vertical inner surface configured to receive a bolster for contacting and stabilizing said patient, while permitting said patient to change orientation respective to the table or bolsters or both, wherein said bolster comprises a bolster shaft having an outer shape configured to reversibly engage one or more of said at least three holes, wherein the bolster shaft perpendicularly traverses said table when said bolster shaft is reversibly engaged with one or more of said at least three, and wherein said bolster shaft possesses an end that is flush with a lower surface of said table or wherein said bolster shaft protrudes from said lower surface of said table when engaged with one or more of said at least three holes, and further wherein said bolster is capable of reversibly engaging any of said at least three holes such that when said bolster is reversibly engaged, said bolster does not circumferentially rotate and does not vertically move, and further comprising a planar member disposed beneath and in spaced apart relation to the bottom surface of the table to form a chamber for receiving air flow generated by an air moving apparatus in fluid communication with the chamber, the planar member having openings at each corner, the openings cut on a radius emanating from the corner, the radius being between two to ten inches.

2. The stabilization table of claim 1, wherein said at least three holes comprise a first hole and a second hole arranged opposite each other along a longitudinal axis of said table and are separated by a width of about 7 inches.

3. The stabilization table of claim 1, wherein said at least three holes comprise a first hole and a second hole generally aligned on either side of a neck of said patient's body.

4. The stabilization table of claim 3 further comprising a third hole and a fourth hole aligned on either side of said patient's hip region.

5. The stabilization table of claim 4 further comprising a fifth hole and a sixth hole aligned on either side of said patient's armpit region.

6. The stabilization table of claim 5 further comprising a seventh hole and an eighth hole aligned on either side of said patient's waist region.

7. The stabilization table of claim 6 further comprising a ninth hole and a tenth hole aligned on either side of said patient's knee region.

8. The stabilization table of claim 1, wherein said one or more of said at least three bolsters is capable of supporting a lateral force of at least 20 pounds.

9. The stabilization table of claim 1, wherein said bolster possesses a vertical surface of at least 6 inches.

10. The stabilization table of claim 1, wherein said bolster has a circular, triangular, or rectangular cross-section.

11. The stabilization table of claim 1, wherein said bolster has a low shear surface.

12. The stabilization table of claim 1, wherein said holes are cylindrical.

13. The stabilization table of claim 1, further comprising a connector.

14. The stabilization table of claim 1, wherein said at least three holes are non-cylindrical holes.

15. The stabilization table of claim 1, wherein said bolsters are locked into one or more of said at least three holes, and wherein the stabilization table further comprises a plurality of bolsters.

16. A method of stabilizing a patient comprising:
selecting a patient in need of therapeutic manipulation;
providing a stabilization table for receiving the patient in a position, wherein the table possesses at least three holes;
providing at least one bolster, wherein the bolster comprises a bolster shaft; and
disposing the at least one bolster within at least one of the at least three holes based on the therapeutic manipulation needed, such that the patient is contacted by the at least one bolster and stabilized based on the contact, while allowing the patient to change orientation respective to the table or the at least one bolster or both, wherein the disposing is a compressive engagement between the bolster shaft of the at least one bolster with one or more of the at least three holes, and wherein the bolster shaft possesses an end that is flush with a lower surface of the table or wherein the bolster shaft protrudes from the lower surface when compressively engaged with one or more of the at least three holes, and wherein the compressively engaged bolster does not circumferentially rotate and does not vertically move; and,
providing a planar member disposed beneath and in spaced apart relation to the lower surface of the table to form a chamber for receiving air flow generated by an air moving apparatus in fluid communication with the chamber, the planar member having openings at each corner, the openings cut on a radius emanating from the corner, the radius being between two to ten inches.

17. The method of claim 16 further comprising disengaging one or more of the bolsters from one or more of the holes and reengaging the one or more disengaged bolsters with a different hole.

18. The method of claim 16 further comprising directing therapeutic force to the patient by applying the force to the at least one bolster.

19. The method of claim 16 further comprising altering the position of the patient relative to the one or more bolsters.

20. The method of claim 16, wherein the therapeutic manipulation is selected from the group consisting of physical therapy, chiropractic manipulations, athletic training, massage therapy and orthopedic therapy.

* * * * *